(12) United States Patent
Kozhukh et al.

(10) Patent No.: US 9,404,193 B1
(45) Date of Patent: Aug. 2, 2016

(54) REACTION PRODUCTS OF GUANIDINE COMPOUNDS OR SALTS THEREOF, POLYEPOXIDES AND POLYHALOGENS

(71) Applicant: Rohm and Haas Electronic Materials LLC, Marlborouh, MA (US)

(72) Inventors: Julia Kozhukh, Cambridge, MA (US); Zuhra I. Niazimbetova, Westborough, MA (US); Maria Anna Rzeznik, Shrewbury, MA (US)

(73) Assignee: Rohm and Haas Electronic Materials LLC

( * ) Notice: Subject to any disclaimer, the term of this patent is extended or adjusted under 35 U.S.C. 154(b) by 0 days.

(21) Appl. No.: 15/079,533

(22) Filed: Mar. 24, 2016

Related U.S. Application Data

(62) Division of application No. 14/086,951, filed on Nov. 21, 2013.

(51) Int. Cl.
| | | |
|---|---|---|
| *C25D 3/32* | (2006.01) | |
| *C25D 3/38* | (2006.01) | |
| *C25D 3/02* | (2006.01) | |
| *C25D 3/56* | (2006.01) | |
| *C25D 5/54* | (2006.01) | |
| *C25D 5/56* | (2006.01) | |
| *H05K 3/18* | (2006.01) | |
| *H05K 3/42* | (2006.01) | |
| *C25D 5/02* | (2006.01) | |

(52) U.S. Cl.
CPC .. *C25D 3/32* (2013.01); *C25D 3/02* (2013.01); *C25D 3/38* (2013.01); *C25D 3/56* (2013.01); *C25D 5/02* (2013.01); *C25D 5/54* (2013.01); *C25D 5/56* (2013.01); *H05K 3/188* (2013.01); *H05K 3/424* (2013.01)

(58) Field of Classification Search
CPC .. C07C 279/08; C07C 335/24; C07C 311/64; C07D 303/10; C25D 3/60; C25D 3/123; C25D 3/565; C25D 3/32; C25D 3/38; H05K 3/188; H05K 3/424; H05K 2201/09509; H05K 2201/09503
See application file for complete search history.

(56) References Cited

U.S. PATENT DOCUMENTS

| | | | |
|---|---|---|---|
| 3,211,751 A | 10/1965 | Batzer et al. | |
| 3,300,395 A | 1/1967 | Michael et al. | |
| 4,311,753 A | 1/1982 | Pucci | |
| 4,327,143 A | 4/1982 | Alvino et al. | |
| 4,550,129 A | 10/1985 | Nir, Jr. | |
| 4,833,204 A | 5/1989 | Yusa et al. | |
| 7,374,652 B2 | 5/2008 | Hayashi et al. | |
| 7,662,981 B2 | 2/2010 | Wang et al. | |
| 7,842,762 B2 | 11/2010 | Zawacky et al. | |
| 2011/0139626 A1 | 6/2011 | Saito et al. | |
| 2011/0171491 A1* | 7/2011 | Suzuki | C25D 1/04 428/687 |
| 2011/0220514 A1* | 9/2011 | Niazimbetova | C07D 233/02 205/297 |

FOREIGN PATENT DOCUMENTS

| | | |
|---|---|---|
| EP | 1741804 | 1/2007 |
| GB | 1500971 | 2/1978 |

OTHER PUBLICATIONS

Search report from corresponding Taiwan 103140403 application, dated Nov. 13, 2015.
Search report from corresponding European 14194281 application, dated May 22, 2015.

* cited by examiner

*Primary Examiner* — Randy Gulakowski
*Assistant Examiner* — Ha S Nguyen
(74) *Attorney, Agent, or Firm* — John J. Piskorski

(57) ABSTRACT

Reaction products of guanidine compounds or salts thereof, polyepoxide compounds and polyhalogen compounds may be used as levelers in metal electroplating baths, such as copper electroplating baths, to provide good throwing power. Such reaction products may plate with good surface properties of the metal deposits and good physical reliability.

9 Claims, No Drawings

REACTION PRODUCTS OF GUANIDINE COMPOUNDS OR SALTS THEREOF, POLYEPOXIDES AND POLYHALOGENS

The present application is a divisional application of copending parent patent application Ser. No. 14/086,951, filed on Nov. 21, 2013.

FIELD OF THE INVENTION

The present invention is directed to reaction products of guanidine compounds or salts thereof, polyepoxide compounds and polyhalogen compounds for use in metal electroplating baths. More specifically, the present invention is directed to reaction products of guanidine compounds or salts thereof, polyepoxide compounds and polyhalogen compounds for use in metal electroplating baths as levelers with good throwing power.

BACKGROUND OF THE INVENTION

Methods for electroplating articles with metal coatings generally involve passing a current between two electrodes in a plating solution where one of the electrodes is the article to be plated. A typical acid copper plating solution includes dissolved copper, usually copper sulfate, an acid electrolyte such as sulfuric acid in an amount sufficient to impart conductivity to the bath, a source of halide, and proprietary additives to improve the uniformity of the plating and the quality of the metal deposit. Such additives include levelers, accelerators and suppressors, among others.

Electrolytic copper plating solutions are used in a variety of industrial applications, such as decorative and anticorrosion coatings, as well as in the electronics industry, particularly for the fabrication of printed circuit boards and semiconductors. For circuit board fabrication, typically, copper is electroplated over selected portions of the surface of a printed circuit board, into blind vias and trenches and on the walls of through-holes passing between the surfaces of the circuit board base material. The exposed surfaces of blind vias, trenches and through-holes, i.e. the walls and the floor, are first made conductive, such as by electroless metal plating, before copper is electroplated on surfaces of these apertures. Plated through-holes provide a conductive pathway from one board surface to the other. Vias and trenches provide conductive pathways between circuit board inner layers. For semiconductor fabrication, copper is electroplated over a surface of a wafer containing a variety of features such as vias, trenches or combinations thereof. The vias and trenches are metallized to provide conductivity between various layers of the semiconductor device.

It is well known in certain areas of plating, such as in electroplating of printed circuit boards ("PCBs"), that the use of levelers in the electroplating bath can be crucial in achieving a uniform metal deposit on a substrate surface. Electroplating a substrate having irregular topography can pose difficulties. During electroplating a voltage drop typically occurs within apertures in a surface which can result in an uneven metal deposit between the surface and the apertures. Electroplating irregularities are exacerbated where the voltage drop is relatively extreme, that is, where the apertures are narrow and tall. Consequently, a metal layer of substantially uniform thickness is frequently a challenging step in the manufacture of electronic devices. Leveling agents are often used in copper plating baths to provide substantially uniform, or level, copper layers in electronic devices.

The trend of portability combined with increased functionality of electronic devices has driven the miniaturization of PCBs. Conventional multilayer PCBs with through-hole interconnects are not always a practical solution. Alternative approaches for high density interconnects have been developed, such as sequential build up technologies, which utilize blind vias. One of the objectives in processes that use blind vias is the maximizing of via filling while minimizing thickness variation in the copper deposit between the vias and the substrate surface. This is particularly challenging when the PCB contains both through-holes and blind vias.

Leveling agents are used in copper plating baths to level the deposit across the substrate surface and to improve the throwing power of the electroplating bath. Throwing power is defined as the ratio of the through-hole center copper deposit thickness to its thickness at the surface. Newer PCBs are being manufactured that contain both through-holes and blind vias. Current bath additives, in particular current leveling agents, do not always provide level copper deposits between the substrate surface and filled through-holes and blind vias. Via fill is characterized by the difference in height between the copper in the filled via and the surface. Accordingly, there remains a need in the art for leveling agents for use in metal electroplating baths for the manufacture of PCBs that provide level copper deposits while bolstering the throwing power of the bath.

SUMMARY OF THE INVENTION

Compounds include reaction products of one or more guanidine compounds or salts thereof, one or more polyepoxide compounds and one or more polyhalogen compounds.

Compositions include one or more sources of metal ions, an electrolyte and one or more compounds of reaction products of one or more guanidine compounds or salts thereof, one or more polyepoxide compounds and one or more polyhalogen compounds.

Methods include providing a substrate; providing a composition including one or more sources of metal ions, and one or more compounds of reaction products of one or more guanidine compounds or salts thereof, one or more polyepoxide compounds and one or more polyhalogen compounds; contacting the substrate with the composition; applying a current to the substrate and composition; and plating a metal on the substrate.

The compounds provide metal layers having a substantially level surface across a substrate, even on substrates having small features and on substrates having a variety of feature sizes. The plating methods effectively deposit metals in blind vias and through-holes such that the metal plating compositions have good throwing power. In addition, metal deposits have good physical reliability in response to thermal shock stress tests.

DETAILED DESCRIPTION OF THE INVENTION

As used throughout this specification the following abbreviations shall have the following meanings unless the context clearly indicates otherwise: A=amperes; $A/dm^2$=amperes per square decimeter; ° C.=degrees Centigrade; g=gram; ppm=parts per million; L=liter, μm=micron=micrometer; mm=millimeters; cm=centimeters; DI=deionized; mL=milliliter; Mw=weight average molecular weight; and Mn=number average molecular weight. All numerical ranges are inclusive and combinable in any order, except where it is clear that such numerical ranges are constrained to add up to 100%.

As used throughout the specification, "feature" refers to the geometries on a substrate. "Aperture" refers to recessed features including through-holes and blind vias. As used throughout this specification, the term "plating" refers to metal electroplating. "Guanidine compounds" means guanidine and derivatives of guanidine. "Deposition" and "plating" are used interchangeably throughout this specification. "Halide" refers to fluoride, chloride, bromide and iodide. "Leveler" refers to an organic compound that is capable of providing a substantially level or planar metal layer. The terms "leveler" and "leveling agent" are used interchangeably throughout this specification. "Accelerator" refers to an organic additive that increases the plating rate of the electroplating bath. "Suppressor" refers to an organic additive that suppresses the plating rate of a metal during electroplating. The terms "printed circuit boards" and "printed wiring boards" are used interchangeably throughout this specification. The term "moiety" means a part of a molecule or polymer that may include either whole functional groups or parts of functional groups as substructures. The articles "a" and "an" refer to the singular and the plural.

Compounds are reaction products of one or more guanidine compounds or salts thereof, one or more polyepoxide compounds and one or more polyhalogen compounds. Guanidine compounds include but are not limited to compounds having formula:

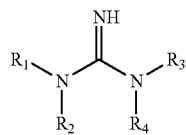

(I)

where $R_1$, $R_2$, $R_3$ and $R_4$ are the same or different and include, but are not limited to: hydrogen; linear or branched, substituted or unsubstituted $(C_1-C_{10})$alkyl; linear or branched carboxy$(C_1-C_{10})$alkyl; linear or branched, substituted or unsubstituted amino$(C_1-C_{10})$alkyl; substituted or unsubstituted aryl; linear or branched, substituted or unsubstituted aryl$(C_1-C_{10})$alkyl; substituted or unsubstituted sulfonyl; —N$(R_5)_2$ where $R_5$ may be the same or different and is hydrogen or linear or branched, substituted of unsubstituted $(C_1-C_{10})$ alkyl; a moiety having formula:

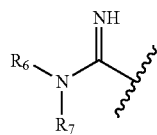

(II)

where $R_6$ and $R_7$ are the same or different and include, but are not limited to: hydrogen; linear or branched, substituted or unsubstituted $(C_1-C_{10})$alkyl; —N$(R_5)_2$ where $R_5$ is defined as above; linear or branched carboxy$(C_1-C_{10})$alkyl; substituted or unsubstituted aryl; substituted or unsubstituted, linear or branched aryl$(C_1-C_{10})$alkyl; a moiety having formula:

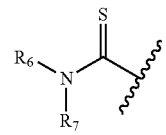

(III)

where $R_6$ and $R_7$ are as defined above. Preferably, $R_1$, $R_2$, $R_3$ and $R_4$ are the same or different and are chosen from hydrogen; linear or branched, substituted or unsubstituted $(C_1-C_5)$ alkyl; linear or branched carboxy$(C_1-C_5)$alkyl; linear or branched, substituted or unsubstituted amino$(C_1-C_5)$alkyl; substituted or unsubstituted phenyl; linear or branched, substituted or unsubstituted phenyl$(C_1-C_5)$alkyl; —N$(R_5)_2$ where $R_5$ is the same or different and is hydrogen, or substituted or unsubstituted, linear or branched $(C_1-C_5)$alkyl; the moiety of formula (II); and salts of formula (I). More preferably, $R_1$, $R_2$, $R_3$ and $R_4$ are the same or different and are chosen from hydrogen; linear or branched, substituted or unsubstituted $(C_1-C_4)$alkyl; linear or branched carboxy$(C_1-C_4)$alkyl; linear or branched, substituted or unsubstituted amino$(C_1-C_4)$alkyl; substituted or unsubstituted phenyl; —N$(R_5)_2$ where $R_5$ is the same or different and is hydrogen or linear or branched, substituted or unsubstituted $(C_1-C_4)$alkyl; the moiety of formula (II); and salts of formula (I). Most preferably, $R_1$, $R_2$, $R_3$ and $R_4$ are the same or different and are chosen from hydrogen; substituted or unsubstituted $(C_1-C_2)$ alkyl; substituted or unsubstituted amino$(C_1-C_2)$alkyl; substituted or unsubstituted phenyl; —N$(R_5)_2$ where $R_5$ is the same or different and is hydrogen or substituted of unsubstituted $(C_1-C_2)$alkyl; carboxy$(C_1-C_2)$alkyl; the moiety of formula (II); and salts of formula (I).

Guanidine salts include, but are not limited to salts having formula:

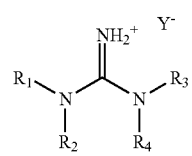

(IV)

where $R_1$, $R_2$, $R_3$ and $R_4$ are as defined above and Y⁻ is a counter anion which includes, but is not limited to: halide, sulfate, hydrogen sulfate, carbonate, bicarbonate, nitrate, nitrite, borate, perchlorate, phosphite or phosphate. Preferably, Y⁻ is halide, sulfate, hydrogen sulfate, nitrate, carbonate or bicarbonate. More preferably, Y⁻ is halide, sulfate, hydrogen sulfate, carbonate or bicarbonate. Most preferably, Y⁻ is halide, sulfate or bicarbonate. Halides are chosen from chloride, bromide, fluoride and iodide. Preferably, the halide is chloride, bromide or iodide. More preferably the halide is chloride or bromide.

Substituent groups on the R variables include, but are not limited to: hydroxyl; linear or branched hydroxy$(C_1-C_5)$ alkyl; mercapto; linear or branched mercapto$(C_1-C_5)$alkyl; linear or branched $(C_1-C_5)$alkyl; carboxy$(C_1-C_5)$alkyl; phenyl; phenyl$(C_1-C_5)$alkyl; —N(R')$_b$ where R' is the same or different and includes, but is not limited to: hydrogen or $(C_1-C_5)$alkyl and b is an integer of 2 to 3. Preferably, substituent groups are chosen from hydroxyl; hydroxy$(C_1-C_2)$alkyl; mercapto; mercapto$(C_1-C_2)$alkyl; $(C_1-C_2)$alkyl; phenyl and —N(R')$_b$ where R' is the same or different and includes, but is not limited to: hydrogen or $(C_1-C_2)$alkyl and b is an integer of 2 to 3. More preferably the substituent groups are chosen from hydroxyl; mercapto; $(C_1-C_2)$alkyl and $—N(R')_b$ where R' is the same or different and includes, but is not limited to: hydrogen or methyl and b is an integer of 2 to 3.

Polyepoxide compounds which may be used are those having 2 or more epoxide moieties joined together by a linkage. Such polyepoxide compounds include, but are not limited to, compounds having formula:

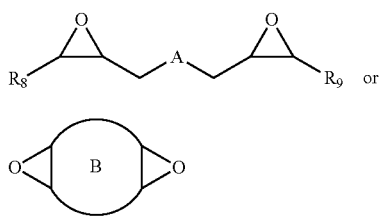

(V)

(VI)

where $R_8$ and $R_9$ are independently chosen from hydrogen and $(C_1-C_4)$alkyl; $A=OR_{10}$ or $R_{11}$; $R_{10}=((CR_{12}R_{13})_m O)$, $(aryl-O)_p$, $CR_{12}R_{13}—Z—CR_{12}CR_{13}$, or $OZ'_t O$; $R_{11}=(CH_2)_y$; B is $(C_5-C_{12})$cycloalkyl; Z=a 5- or 6-membered ring; Z' is $R_{14}OArOR_{14}$, $(R_{15}O)_a Ar(OR_{15})$, or $(R_{15}O)_a$, $Cy(OR_{15})$, $Cy=(C_5-C_{12})$cycloalkyl; each $R_{12}$ and $R_{13}$ are independently chosen from hydrogen, methyl, or hydroxyl; each $R_{14}$ represents $(C_1-C_8)$alkyl; each $R_{15}$ represents a $(C_2-C_6)$alkyleneoxy; each a=1-10; m=1-6; p=1-6; t=1-4; and y=0-6. $R_8$ and $R_9$ are preferably independently chosen from hydrogen and $(C_1-C_2)$alkyl. When $R_8$ and $R_9$ are not joined to form a cyclic compound, it is preferred that $R_8$ and $R_9$ are both hydrogen. When $R_8$ and $R_9$ are joined to form a cyclic compound, it is preferred that A is $R_{11}$ or a chemical bond and that a $(C_5-C_{10})$carbocyclic ring is formed. It is preferred that m=2-4. Phenyl-O is the preferred aryl-O group for $R_{10}$. It is preferred that p=1-4, more preferably 1-3, and still more preferably 1-2. Z is preferably a 5- or 6-membered carbocyclic ring and, more preferably, Z is a 6-membered carbocyclic ring. Preferably, y=0-4, and more preferably, 1-4. When $A=R_{11}$ and y=0, then A is a chemical bond. Preferably, $Z'=R_{14}OArOR_{14}$ or $(R_{15}O)_a Ar(OR_{15})$. Each $R_{14}$ is preferably $(C_1-C_6)$alkyl and more preferably $(C_1-C_4)$alkyl. Each $R_{15}$ is preferably $(C_2-C_4)$alkyleneoxy. It is preferred that t=1-2. Preferably, a=1-8, more preferably, 1-6, and most preferably, 1-4. Each Ar group may be substituted with one or more substituent groups which include, but are not limited to: $(C_1-C_4)$alkyl, $(C_1-C_4)$alkoxy or halogen. Preferably Ar is $(C_6-C_{15})$aryl. Exemplary aryl groups are phenyl, methylphenyl, naphthyl, pyridinyl, bisphenylmethyl and 2,2-bisphenylpropyl. Preferably Cy is $(C_6-C_{15})$cycloalkyl. The $(C_5-C_{12})$cycloalkyl groups for B may be monocyclic, spirocyclic, fused or bicyclic groups. Preferably B is a $(C_5-C_{10})$cycloalkyl, more preferably, cyclooctyl.

Exemplary compounds of formula (V) include, but are not limited to: 1,4-butanediol diglycidyl ether, ethylene glycol diglycidyl ether, diethylene glycol diglycidyl ether, triethylene glycol diglycidyl ether, glycerol diglycidyl ether, neopentyl glycol diglycidyl ether, propylene glycol diglycidyl ether, dipropylene glycol diglycidyl ether and poly(propyleneglycol) diglycidyl ether.

Polyhalogen compounds include halogen containing compounds which include two or more halogens which may react with the one or more guanidine compounds or salts thereof. Such polyhalogen compounds include, but are not limited to, compounds having the following formula:

(VII)

where $X_1$ and $X_2$ may be the same or different and are halogens chosen from chlorine, bromine, fluorine and iodine. Preferably, $X_1$ and $X_2$ are independently chlorine, bromine and iodine. More preferably, $X_1$ and $X_2$ are independently chlorine and bromine. $R_{16}$ is a moiety having formula:

(VIII)

where $R_{17}$ is a linear or branched, substituted or unsubstituted $(C_1-C_{15})$alkyl, substituted or unsubstituted $(C_6-C_{12})$cycloalkyl, substituted or unsubstituted $(C_6-C_{15})$aryl, $—CH_2—O—(R_{18}—O)_q—CH_2—$ where $R_{18}$ is a substituted or unsubstituted, linear or branched $(C_2-C_{10})$alkyl and q is an integer of 1-10. Preferably, $R_{17}$ is a linear or branched, substituted or unsubstituted $(C_1-C_8)$alkyl, substituted or unsubstituted $(C_6-C_8)$cycloalkyl, substituted or unsubstituted phenyl, $—CH_2—O—(R_8—O)_q—CH_2—$ where $R_{18}$ is a substituted or unsubstituted, linear or branched $(C_2-C_8)$alkyl and q is an integer of 1-8. More preferably, $R_{17}$ is a linear or branched, substituted or unsubstituted $(C_1-C_4)$alkyl, substituted or unsubstituted cyclohexyl, phenyl, $—CH_2—O—(R_{18}—O)_q—CH_2—$ where $R_{18}$ is a substituted or unsubstituted $(C_2-C_3)$alkyl and q is an integer of 1-5. Substituent groups include, but are not limited to: halogens, hydroxyl, linear or branched hydroxy$(C_1-C_5)$alkyl or linear or branched $(C_1-C_5)$alkoxy. Preferably, the substituent groups are halogens, hydroxyl or linear or branched $(C_1-C_5)$alkoxy. More preferably the substituents are hydroxyl or linear or branched $(C_1-C_5)$alkyl. Most preferably the substituents are linear or branched $(C_1-C_3)$alkyl.

Examples of such polyhalogens are 1,2-dibromoethane; 1,2-dichloroethane; 1,2-diiodoethane; 1,3-dibromopropane; 1,3-dichloropropane; 1,3-diiodopropane; 1,4-dibromobutane; 1,4-dichlorobutane; 1,4-diiodobutane; 1,5-dibromopentane; 1,5-dichloropentane; 1,5-diiodopentane; 1,6-dibromohexane; 1,6-dichlorohexane; 1,6-diiodohexane; 1,7-dibromoheptane; 1,7-dichloroheptane; 1,7-diiodoheptane; 1,8-dibromooctane; 1,8-dichlorooctane; 1,8-diiodooctane; 1,3-dichloro-2-propanol; 1,4-dichloro-2,3-butanediol; 1-bromo-3-chloroethane; 1-chloro-3-iodoethane; 1,2,3-trichloropropane; 1-bromo-3-chloropropane; 1-chloro-3-iodopropane; 1,4-dichloro-2-butanol; 2,3-dichloro-1-propanol; 1,4-dichlorocyclohexane; 1-bromo-3-chloro-2-methylpropane; 1,5-dichloro[3-(2-chloroethyl)]pentane; 1,10-dichlorodecane; 1,18-dichloroooctadecane; 2,2'-dichloroethyl ether; 1,2-bis(2-chloroethoxy)ethane; diethylene glycol bis(2-chloroethyl)ether; triethylene glycol bis(2-chloroethyl)ether; 2,2'-dichloropropyl ether; 2,2'-dichlorobutyl ether; tetraethylene glycol bis(2-bromoethyl) ether and heptaethylene glycol bis(2-chloroethyl) ether.

One or more guanidine compounds or salts thereof are typically suspended in isopropanol at 80° C. with dropwise addition of a mixture of one or more polyepoxides and one or more polyhalogens. The temperature of the heating bath is then increased from 80° C. to 95° C. Heating with stirring is done for 2 hours to 8 hours. The temperature of the heating bath is then reduced to room temperature with stirring for 12 hours to 24 hours. The amounts for each component may vary but, in general, sufficient amount of each reactant is added to provide a product where the molar ratio of the moiety from the guanidine or salt thereof to the moiety from the polyepoxide to the moiety from the polyhalogen ranges from 0.5-1: 0.5-1:0.05-0.5 based on monomer molar ratios.

The plating compositions and methods which include one or more of the reaction products are useful in providing a substantially level plated metal layer on a substrate, such as a printed circuit board or semiconductor chip. Also, the plating compositions and methods are useful in filling apertures in a substrate with metal. The metal deposits have good throwing power and good physical reliability in response to thermal shock stress tests.

Any substrate upon which metal can be electroplated may be used as a substrate with the metal plating compositions containing the reaction products. Such substrates include, but are not limited to: printed wiring boards, integrated circuits, semiconductor packages, lead frames and interconnects. An integrated circuit substrate may be a wafer used in a dual damascene manufacturing process. Such substrates typically contain a number of features, particularly apertures, having a variety of sizes. Through-holes in a PCB may have a variety of diameters, such as from 50 μm to 350 μm in diameter. Such through-holes may vary in depth, such as from 0.8 mm to 10 mm. PCBs may contain blind vias having a wide variety of sizes, such as up to 200 μm diameter and 150 μm depth, or greater.

Conventional metal plating compositions may be used. The metal plating compositions contain a source of metal ions, an electrolyte, and a leveling agent, where the leveling agent is a reaction product of one or more guanidine compounds or salts thereof, one or more polyepoxide compounds and one or more polyhalogen compounds. The metal plating compositions may contain a source of halide ions, an accelerator and a suppressor. Metals which may be electroplated from the compositions include, but are not limited to, copper, tin and tin/copper alloys.

Suitable copper ion sources are copper salts and include without limitation: copper sulfate; copper halides such as copper chloride; copper acetate; copper nitrate; copper tetrafluoroborate; copper alkylsulfonates; copper aryl sulfonates; copper sulfamate; copper perchlorate and copper gluconate. Exemplary copper alkane sulfonates include copper ($C_1$-$C_6$)alkane sulfonate and more preferably copper ($C_1$-$C_3$)alkane sulfonate. Preferred copper alkane sulfonates are copper methanesulfonate, copper ethanesulfonate and copper propanesulfonate. Exemplary copper arylsulfonates include, without limitation, copper benzenesulfonate and copper p-toluenesulfonate. Mixtures of copper ion sources may be used. One or more salts of metal ions other than copper ions may be added to the present electroplating baths. Typically, the copper salt is present in an amount sufficient to provide an amount of copper metal of 10 to 400 g/L of plating solution.

Suitable tin compounds include, but are not limited to salts, such as tin halides, tin sulfates, tin alkane sulfonate such as tin methane sulfonate, tin aryl sulfonate such as tin benzenesulfonate and tin p-toluenesulfonate. The amount of tin compound in these electrolyte compositions is typically an amount that provides a tin content in the range of 5 to 150 g/L. Mixtures of tin compounds may be used in an amount as described above.

The electrolyte useful in the present invention may be alkaline or acidic. Typically the electrolyte is acidic. Suitable acidic electrolytes include, but are not limited to, sulfuric acid, acetic acid, fluoroboric acid, alkanesulfonic acids such as methanesulfonic acid, ethanesulfonic acid, propanesulfonic acid and trifluoromethane sulfonic acid, aryl sulfonic acids such as benzenesulfonic acid p-toluenesulfonic acid, sulfamic acid, hydrochloric acid, hydrobromic acid, perchloric acid, nitric acid, chromic acid and phosphoric acid. Mixtures of acids may be advantageously used in the present metal plating baths. Preferred acids include sulfuric acid, methanesulfonic acid, ethanesulfonic acid, propanesulfonic acid, hydrochloric acid and mixtures thereof. The acids may be present in an amount in the range of from 1 to 400 g/L. Electrolytes are generally commercially available from a variety of sources and may be used without further purification.

Such electrolytes may optionally contain a source of halide ions. Typically chloride ions are used. Exemplary chloride ion sources include copper chloride, tin chloride, sodium chloride, potassium chloride and hydrochloric acid. A wide range of halide ion concentrations may be used in the present invention. Typically, the halide ion concentration is in the range of from 0 to 100 ppm based on the plating bath. Such halide ion sources are generally commercially available and may be used without further purification.

The plating compositions typically contain an accelerator. Any accelerators (also referred to as brightening agents) are suitable for use in the present invention. Such accelerators are well-known to those skilled in the art. Accelerators include, but are not limited to, N,N-dimethyl-dithiocarbamic acid-(3-sulfopropyl)ester; 3-mercapto-propylsulfonic acid-(3-sulfopropyl)ester; 3-mercapto-propylsulfonic acid sodium salt; carbonic acid-dithio-o-ethylester-s-ester with 3-mercapto-1-propane sulfonic acid potassium salt; bis-sulfopropyl disulfide; bis-(sodium sulfopropyl)-disulfide; 3-(benzothiazolyl-S-thio)propyl sulfonic acid sodium salt; pyridinium propyl sulfobetaine; 1-sodium-3-mercaptopropane-1-sulfonate; N,N-dimethyl-dithiocarbamic acid-(3-sulfoethyl)ester; 3-mercapto-ethyl propylsulfonic acid-(3-sulfoethyl)ester; 3-mercapto-ethylsulfonic acid sodium salt; carbonic acid-dithio-o-ethylester-s-ester with 3-mercapto-1-ethane sulfonic acid potassium salt; bis-sulfoethyl disulfide; 3-(benzothiazolyl-S-thio)ethyl sulfonic acid sodium salt; pyridinium ethyl sulfobetaine; and 1-sodium-3-mercaptoethane-1-sulfonate. Accelerators may be used in a variety of amounts. In general, accelerators are used in an amount of 0.1 ppm to 1000 ppm.

Any compound capable of suppressing the metal plating rate may be used as a suppressor in the present electroplating compositions. Suitable suppressors include, but are not limited to, polypropylene glycol copolymers and polyethylene glycol copolymers, including ethylene oxide-propylene oxide ("EO/PO") copolymers and butyl alcohol-ethylene oxide-propylene oxide copolymers. Suitable butyl alcohol-ethylene oxide-propylene oxide copolymers are those having a weight average molecular weight of 100 to 100,000, preferably 500 to 10,000. When such suppressors are used, they are typically present in an amount in the range of from 1 to 10,000 ppm based on the weight of the composition, and more typically from 5 to 10,000 ppm. The leveling agents of the present invention may also possess functionality capable of acting as suppressors.

In general, the reaction products have a number average molecular weight (Mn) of 200 to 10,000, typically from 300 to 50,000, preferably from 500 to 8000, although reaction products having other Mn values may be used. Such reaction products may have a weight average molecular weight (Mw) value in the range of 1000 to 50,000, typically from 5000 to 30,000, although other Mw values may be used.

The amount of the reaction product (leveling agent) used in the metal electroplating compositions depends upon the particular leveling agents selected, the concentration of the metal ions in the electroplating composition, the particular electrolyte used, the concentration of the electrolyte and the current density applied. In general, the total amount of the leveling agent in the electroplating composition ranges from 0.01 ppm to 500 ppm, preferably from 0.1 ppm to 250 ppm, most preferably from 0.5 ppm to 100 ppm, based on the total weight of the plating composition, although greater or lesser amounts may be used.

The electroplating compositions may be prepared by combining the components in any order. It is preferred that the inorganic components such as source of metal ions, water, electrolyte and optional halide ion source are first added to the bath vessel, followed by the organic components such as leveling agent, accelerator, suppressor, and any other organic component.

The electroplating compositions may optionally contain at least one additional leveling agent. Such additional leveling agents may be another leveling agent of the present invention, or alternatively, may be any conventional leveling agent. Suitable conventional leveling agents that can be used in combination with the present leveling agents include, without limitations, those disclosed in U.S. Pat. No. 6,610,192 to Step et al., U.S. Pat. No. 7,128,822 to Wang et al., U.S. Pat. No. 7,374,652 to Hayashi et al. and U.S. Pat. No. 6,800,188 to Hagiwara et al. Such combination of leveling agents may be used to tailor the characteristics of the plating bath, including leveling ability and throwing power.

Typically, the plating compositions may be used at any temperature from 10 to 65° C. or higher. Preferably, the temperature of the plating composition is from 10 to 35° C. and more preferably from 15 to 30° C.

In general, the metal electroplating compositions are agitated during use. Any suitable agitation method may be used and such methods are well-known in the art. Suitable agitation methods include, but are not limited to: air sparging, work piece agitation, and impingement.

Typically, a substrate is electroplated by contacting the substrate with the plating composition. The substrate typically functions as the cathode. The plating composition contains an anode, which may be soluble or insoluble. Potential is typically applied to the electrodes. Sufficient current density is applied and plating performed for a period of time sufficient to deposit a metal layer having a desired thickness on the substrate as well as to fill blind vias, trenches and through-holes, or to conformally plate through-holes. Current densities may range from 0.05 to 10 A/dm$^2$, although higher and lower current densities may be used. The specific current density depends in part upon the substrate to be plated, the composition of the plating bath, and the desired surface metal thickness. Such current density choice is within the abilities of those skilled in the art.

An advantage of the present invention is that substantially level metal deposits are obtained on a PCB. Through-holes and/or blind vias in the PCB are substantially filled. A further advantage of the present invention is that a wide range of apertures and aperture sizes may be filled or conformally plated with desirable throwing power.

Throwing power is defined as the ratio of the average thickness of the metal plated in the center of a through-hole compared to the average thickness of the metal plated at the surface of the PCB sample and is reported as a percentage. The higher the throwing power, the better the plating composition is able to conformally plate the through-hole. Metal plating compositions of the present invention have a throwing power of ≥65%, preferably ≥70%.

The compounds provide metal layers having a substantially level surface across a substrate, even on substrates having small features and on substrates having a variety of feature sizes. The plating methods effectively deposit metals in through-holes such that the metal plating compositions have good throwing power.

While the methods of the present invention have been generally described with reference to printed circuit board manufacture, it is appreciated that the present invention may be useful in any electrolytic process where an essentially level or planar metal deposit and filled or conformally plated apertures are desired. Such processes include semiconductor packaging and interconnect manufacture.

The following examples are intended to further illustrate the invention but are not intended to limit its scope.

Example 1

Guanidine hydrochloride (9.56 g, 0.1 mol) was suspended in 20 mL isopropanol in a 100 mL round-bottom, three-neck flask equipped with condenser, thermometer, and stir bar at 80° C. 1,4-Butanediol diglycidyl ether (12.13 g, 0.060 mol) and 1,4-dibromobutane (0.71 g, 0.003 mol) were mixed together and added dropwise to the solution, and the vial containing the 1,4-butanediol diglycidyl ether and 1,4-dibromobutane was rinsed with 2 mL isopropanol. The heating bath temperature was increased to 95° C. The resulting mixture was heated for 4 hours, then left to stir at room temperature overnight. The reaction mixture was rinsed with water into a polyethylene bottle for storage and 50% sulfuric acid (10.8 g) was added to solubilize the reaction product. The molar ratio of guanidine moiety to epoxide moiety to aliphatic moiety from the dihalogen was 1:0.6:0.03 based on monomer molar ratios.

Example 2

Guanidine hydrochloride (9.53 g, 0.1 mol) was suspended in 20 mL isopropanol in a 100 mL round-bottom, three-neck flask equipped with condenser, thermometer, and stir bar at 80° C. 1,4-Butanediol diglycidyl ether (12.11 g, 0.06 mol) was added dropwise to the solution, and the vial containing the 1,4-butanediol diglycidyl ether was rinsed with 2 mL isopropanol. The heating bath temperature was increased to 95° C. The resulting mixture was heated for 4 hours and 1,4-dibromobutane (0.69 g, 0.003 mol) was added dropwise to the reaction mixture. The oil bath temperature was kept at 95° C. for 1 hour, and then the reaction was left to stir at room temperature overnight. The reaction mixture was rinsed with water into a polyethylene bottle for storage and 50% sulfuric acid (4.6 g) was added to solubilize the reaction product. The molar ratio of guanidine moiety to epoxide moiety to aliphatic moiety from the dihalogen was determined to be 1:0.6: 0.03 based on monomer molar ratios.

Example 3

A plurality of copper electroplating baths were prepared by combining 75 g/L copper as copper sulfate pentahydrate, 240 g/L sulfuric acid, 60 ppm chloride ion, 1 ppm of an accelerator and 1.5 g/L of a suppressor. The accelerator was bis (sodium-sulfopropyl)disulfide. The suppressor was an EO/PO copolymer having a weight average molecular weight of <5,000 and terminal hydroxyl groups. The electroplating baths also contained the reaction product from Example 1 in amounts of 1, 5, 10 or 20 ppm or the reaction product from Example 2 in amounts of 1, 5 or 10 ppm. The reaction products were used without purification.

Example 4

Samples of either a 3.2 mm or a 1.6 mm thick of double-sided FR4 PCBs, 5 cm×9.5 cm, having a plurality of through-holes were electroplated with copper in Haring cells using the copper electroplating baths of Example 3. The 3.2 mm thick samples had 0.3 mm diameter through-holes and the 1.6 mm thick samples had 0.25 mm diameter through-holes. The temperature of each bath was 25° C. A current density of 2.16 A/dm$^2$ was applied to the 3.2 mm samples for 80 minutes and a current density of 3.24 A/dm$^2$ was applied to the 1.6 mm samples for 44 minutes. The copper baths that included the reaction products from Example 1 were only used to plate the PCBs which were 1.6 mm thick. The copper baths that included the reaction product of Example 2 were used to plate copper on both the 3.2 mm and the 1.6 mm PCBs. The copper plating process was repeated using the copper baths containing the reaction product of Example 2 on both types of PCBs. The copper plated samples were analyzed to determine the throwing power ("TP") of the plating bath, and percent cracking according to the following methods.

Throwing power was calculated by determining the ratio of the average thickness of the metal plated in the center of a through-hole compared to the average thickness of the metal plated at the surface of the PCB sample. The throwing power is reported in Table 1 as a percentage.

The percent cracking was determined according to the industry standard procedure, IPC-TM-650-2.6.8. Thermal Stress, Plated-Through Holes, published by IPC (Northbrook, Ill., USA), dated May, 2004, revision E.

TABLE 1

| Reaction Product | Panel Thickness in mm | Leveler Concentration in ppm | TP (%) | Cracking % |
|---|---|---|---|---|
| Example 1 | 1.6 | 1 | 81 | 0 |
|  | 1.6 | 5 | 80 | 0 |
|  | 1.6 | 10 | 71 | 0 |
|  | 1.6 | 20 | 76 | 5 |
| Example 2 | 1.6 | 1 | 101 | 0 |
|  | 1.6 | 5 | 80 | 0 |
|  | 1.6 | 10 | 80 | 0 |
|  | 1.6 | 20 | 79 | 0 |
|  | 3.2 | 1 | 87 | 0 |
|  | 3.2 | 5 | 76 | 0 |
|  | 3.2 | 10 | 85 | 0 |

The results showed that the throwing power exceeded 70% indicating superior throwing power performance for the reaction products of Examples 1 and 2. In addition, cracking was observed only in one sample copper plated with the reaction product of Example 1. The lower the percentage of cracking, the better is the plating performance.

Examples 5-9

Five reaction products were prepared according to the method described in Example 1 except that the molar ratios of the monomers were varied as disclosed in Table 2 below.

TABLE 2

| Reaction Product | Guanidine Hydrochloride ($M_1$) | 1,4-butanediol diglycidyl ether ($M_2$) | 1,4-dibromobutane ($M_3$) |
|---|---|---|---|
| Example 5 | 1 | 0.5 | 0.06 |
| Example 6 | 1 | 0.5 | 0.13 |
| Example 7 | 1 | 0.44 | 0.19 |
| Example 8 | 1 | 0.38 | 0.25 |
| Example 9 | 1 | 0.32 | 0.32 |

Example 10

Guanidine hydrochloride (4.78 g, 0.05 mol) and diphenylguanidine (10.50 g, 0.05 mol) were suspended in 20 mL isopropanol in a 100 ml, round-bottom, three-neck flask equipped with condenser, thermometer, and stir bar at 80° C. 1,4-Butanediol diglycidyl ether (11.47 g, 0.057 mol) and 1,4-dibromobutane (1.36 g, 0.006 mol) were mixed together and added dropwise to the solution, and the vial containing the 1,4-butanediol diglycidyl ether and 1,4-dibromobutane was rinsed with 3 mL isopropanol. The heating bath temperature was increased to 95° C. The resulting mixture was heated for 4 hours, then left to stir at room temperature overnight. The reaction mixture was rinsed with water into a polyethylene bottle for storage and 50% sulfuric acid (11.5 g) was added to solubilize the reaction product. The molar ratio of guanidine hydrochloride to 1,3-diphenylguanidine to epoxide moiety to aliphatic moiety from the dihalogen was 0.5:0.5:0.57:0.06 based on monomer molar ratios.

Examples 11-28

The compounds of Table 3 are reacted together substantially according to the process described for Examples 5-10 above. The molar ratios of each component are in Table 3.

TABLE 3

| Example | Guanidine Compounds or Salts thereof ($M_1$) | Epoxide ($M_2$) | Dihalogen ($M_3$) | Molar ratio of $M_1:M_2:M_3$ Moieties |
|---|---|---|---|---|
| 11 | H$_2$N–C(=NH$_2^+$ HCO$_3^-$)–NH–NH$_2$ | 1,4-Butanediol diglyciyl ether | 1,4-dibromobutane | 1:0.57:0.06 |
| 12 | (o-tolyl)NH–C(=NH)–NH–C(=NH)–NH$_2$ | 1,4-Butanediol diglycidyl ether | 1,4-dibromobutane | 1:0.57:0.06 |

TABLE 3-continued

| Example | Guanidine Compounds or Salts thereof ($M_1$) | Epoxide ($M_2$) | Dihalogen ($M_3$) | Molar ratio of $M_1:M_2:M_3$ Moieties |
|---|---|---|---|---|
| 13 | N-phenyl biguanide | 1,4-Butanediol diglycidyl ether | 1,4-dibromobutane | 1:0.57:0.06 |
| 14 | diaminoguanidine hydrochloride | 1,4-Butanediol diglycidyl ether | 1,4-dibromobutane | 1:0.57:0.06 |
| 15 | N-phenethyl biguanide hydrochloride | 1,4-Butanediol diglycidyl ether | 1,4-dibromobutane | 1:0.57:0.06 |
| 16 | sulfaguanidine | 1,4-Butanediol diglycidyl ether | 1,4-dibromobutane | 1:0.57:0.06 |
| 17 | agmatine sulfate | 1,4-Butanediol diglycidyl ether | 1,4-dibromobutane | 1:0.57:0.06 |
| 18 | 2-thiobiuret (guanylthiourea) | 1,4-Butanediol diglycidyl ether | 1,4-dibromobutane | 1:0.57:0.06 |
| 19 | 1,1-dimethylguanidine hemisulfate | 1,4-Butanediol diglycidyl ether | 1,4-dibromobutane | 1:0.57:0.06 |
| 20 | guanidine hydrochloride | 1,4-Butanediol diglycidyl ether | 1,4-dichlorobutane | 1:0.57:0.06 |
| 21 | guanidine hydrochloride | 1,4-Butanediol diglycidyl ether | 1,4-diiodobutane | 1:0.57:0.06 |
| 22 | guanidinoacetic acid | 1,4-Butanediol diglycidyl ether | 1,4-dibromobutane | 1:0.57:0.06 |

TABLE 3-continued

| Example | Guanidine Compounds or Salts thereof ($M_1$) | Epoxide ($M_2$) | Dihalogen ($M_3$) | Molar ratio of $M_1:M_2:M_3$ Moieties |
|---|---|---|---|---|
| 23 | 1,3-diphenylguanidine | 1,4-Butanediol diglycidyl ether | 1,4-dibromobutane | 1:0.57:0.06 |
| 24 | 1,3-di(o-tolyl)guanidine | 1,4-Butanediol diglycidyl ether | 1,4-dibromobutane | 1:0.57:0.06 |
| 25 | guanidine hydrochloride | 1,4-Butanediol diglycidyl ether | 1,3-bis(bromomethyl)-benzene | 1:0.57:0.06 |
| 26 | guanidine hydrochloride | 1,4-Butanediol diglycidyl ether | 1,3-bis(bromomethyl)-benzene | 1:0.57:0.06 |
| 27 | guanidine hydrochloride | 1,4-Butanediol diglycidyl ether | 1,3-bis(bromomethyl)-cyclohexane | 1:0.57:0.06 |
| 28 | guanidine hydrochloride | 1,4-Butanediol diglycidyl ether | 1,3-bis(bromomethyl)-cyclohexane | 1:0.57:0.06 |

What is claimed is:

1. A method comprising:
a) providing a substrate;
b) providing a composition comprising one or more sources of metal ions, and one or more compounds comprising a reaction product of one or more guanidine compounds or salts thereof, one or more polyepoxide compounds and one or more polyhalogen compounds, wherein the one or more polyhalogens have a formula:

$$X_1\text{—}R_{16}\text{—}X_2 \quad \text{(VII)}$$

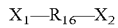

wherein $X_1$ and $X_2$ may be the same or different and are halogens chosen from chlorine, bromine, fluorine and iodine; R16 is a moiety having formula:

$$\text{—}CH_2\text{—}R_{17}\text{—}CH_2\text{—} \quad \text{(VIII)}$$

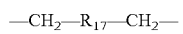

wherein $R_{17}$ is a linear or branched, substituted or unsubstituted ($C_1$-$C_{18}$)alkyl, substituted or unsubstituted ($C_6$-$C_{12}$)cycloalkyl, substituted or unsubstituted (C.sub.6-$C_{15}$)aryl, —$CH_2$—O—($R_{18}$—O)$_q$—$CH_2$— where $R_{18}$ is a substituted or unsubstituted, linear or branched ($C_2$-$C_{10}$)alkyl and q is an integer of 1-10;
c) contacting a substrate with the composition;
d) applying a current to the substrate and the composition; and
e) depositing a metal on the substrate.

2. The method of claim 1, wherein the one or more sources or metal ions are chosen from copper salts and tin salts.

3. The method of claim 1 wherein the substrate comprises a plurality of one or more of through-holes, trenches and vias.

4. The method of claim 1, wherein the one or more guanidine compounds have a formula:

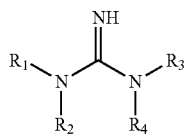

(I)

wherein $R_1$, $R_2$, $R_3$ and $R_4$ are the same or different and comprise hydrogen; linear or branched, substituted or unsubstituted ($C_1$-$C_{10}$)alkyl; linear or branched carboxy ($C_1$-$C_{10}$)alkyl; linear or branched, substituted or unsubstituted amino($C_1$-$C_{10}$)alkyl;

substituted or unsubstituted aryl; linear or branched, substituted or unsubstituted aryl($C_1$-$C_{10}$)alkyl; substituted or unsubstituted sulfonyl; —N($R_5$)$_2$ where $R_5$ may be the same or different and are hydrogen or linear or branched, substituted or unsubstituted ($C_1$-$C_{10}$)alkyl; or a moiety having formula:

(II)

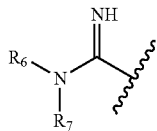

wherein $R_6$ and $R_7$ are the same or different and comprise hydrogen, linear or branched, substituted or unsubstituted $(C_1-C_{10})$alkyl; linear or branched carboxy$(C_1-C_{10})$alkyl; substituted or unsubstituted aryl; substituted or unsubstituted, linear or branched aryl$(C_1-C_{10})$alkyl; —N$(R_5)_2$ where $R_5$ is defined as above; or a moiety having formula:

(III)

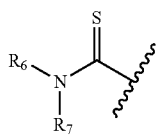

wherein $R_6$ and $R_7$ are as defined above.

5. The method of claim 1, wherein salts of the one or more guanidine compounds have a formula:

(IV)

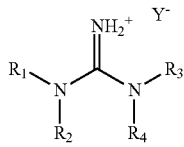

wherein $R_1$, $R_2$, $R_3$ and $R_4$ are as defined in claim 1 and $Y^-$ comprises halide, sulfate, hydrogen sulfate, carbonate, bicarbonate, nitrate, nitrite, borate, perchlorate, phosphite or phosphate.

6. The method of claim 1, wherein the one or more polyepoxides have a formula:

(V)

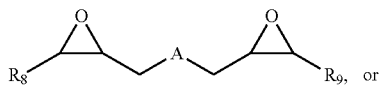

(VI)

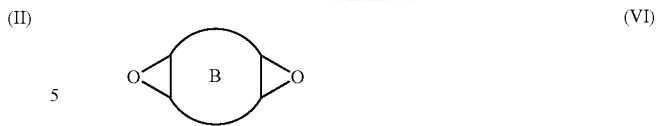

wherein $R_8$ and $R_9$ are the same or different and are chosen from hydrogen and $(C_1-C_4)$alkyl; A=$OR_{10}$ or $R_{11}$; $R_{10}$=((CR$_{12}$R$_{13}$)$_m$O), (aryl-O)$_p$, CR$_{12}$R$_{13}$—Z—CR$_{12}$CR$_{13}$, or OZ'$_t$O; $R_{11}$=(CH$_2$)$_y$; B is $(C_5-C_{12})$cycloalkyl; Z=a 5- or 6-membered ring; Z' is $R_{14}$OArOR$_{14}$, $(R_{15}O)_a$Ar$(OR_{15})$, or $(R_{15}O)_a$, $C_y(OR_{15})$, Cy=$(C_5-C_{12})$cycloalkyl; each $R_{12}$ and $R_{13}$ are the same or different and are chosen from hydrogen, methyl, or hydroxyl; $R_{14}$ is $(C_1-C_8)$ alkyl; $R_{15}$ is $(C_2-C_6)$alkyleneoxy; a=1-10; m=1-6; p=1-6; t=1-4; and y=0-6.

7. The method of claim 1, wherein the one or more polyepoxides are chosen from 1,4-butanediol diglycidyl ether, ethylene glycol diglycidyl ether, diethylene glycol diglycidyl ether, triethylene glycol diglycidyl ether, glycerol diglycidyl ether, neopentyl glycol diglycidyl ether, propylene glycol diglycidyl ether, dipropylene glycol diglycidyl ether and poly(propyleneglycol) diglycidyl ether.

8. The method of claim 1, wherein the one or more polyhalogen compounds are chosen from 1,2-dibromoethane; 1,2-dichloroethane; 1,2-diiodoethane; 1,3-dibromopropane; 1,3-dichloropropane; 1,3-diiodopropane; 1,4-dibromobutane; 1,4-dichlorobutane; 1,4-diiodobutane; 1,5-dibromopentane; 1,5-dichloropentane; 1,5-diiodopentane; 1,6-dibromohexane; 1,6-dichlorohexane; 1,6-diiodohexane; 1,7-dibromoheptane; 1,7-dichloroheptane; 1,7-diiodoheptane; 1,8-dibromooctane; 1,8-dichlorooctane; 1,8-diiodooctane; 1,3-dichloro-2-propanol; 1,4-dichloro-2,3-butanediol; 1-bromo-3-chloroethane; 1-chloro-3-iodoethane; 1,2,3-trichloropropane; 1-bromo-3-chloropropane; 1-chloro-3-iodopropane; 1,4-dichloro-2-butanol; 2,3-dichloro-1-propanol; 1,4-dichlorocyclohexane; 1-bromo-3-chloro-2-methylpropane; 1,5-dichloro[3-(2-chloroethyl)]pentane; 1,10-dichlorodecane; 1,18-dichlorooctadecane; 2,2'-dichloroethyl ether; 1,2-bis(2-chloroethoxy)ethane; diethylene glycol bis(2-chloroethyl)ether; triethylene glycol bis(2-chloroethyl)ether; 2,2'-dichloropropyl ether; 2,2'-dichlorobutyl ether; tetraethylene glycol bis(2-bromoethyl) ether and heptaethylene glycol bis(2-chloroethyl) ether.

9. The method of claim 1, wherein a molar ratio of a moiety of the one or more guanidine compounds or salts thereof to a moiety of the one or more polyepoxide compounds to a moiety of the one or more polyhalogen compounds is from 0.5-1:0.5-1:0.05-0.5 based on monomer molar ratios.

* * * * *